(12) United States Patent
Chetlapalli

(10) Patent No.: US 9,233,018 B2
(45) Date of Patent: Jan. 12, 2016

(54) ORTHOPEDIC DEVICE

(71) Applicant: Ossur hf, Reykjavik (IS)

(72) Inventor: Janaki Ram-srinivasaRao Chetlapalli, Irvine, CA (US)

(73) Assignee: Ossur hf, Reykjavik (IS)

( * ) Notice: Subject to any disclaimer, the term of this patent is extended or adjusted under 35 U.S.C. 154(b) by 256 days.

(21) Appl. No.: 13/836,198

(22) Filed: Mar. 15, 2013

(65) Prior Publication Data

US 2013/0253396 A1    Sep. 26, 2013

Related U.S. Application Data

(60) Provisional application No. 61/613,200, filed on Mar. 20, 2012.

(51) Int. Cl.
*A61F 5/01*    (2006.01)

(52) U.S. Cl.
CPC ............... *A61F 5/0125* (2013.01); *A61F 5/01* (2013.01); *A61F 5/0123* (2013.01); *A61F 2005/0158* (2013.01); *A61F 2005/0167* (2013.01); *A61F 2005/0172* (2013.01)

(58) Field of Classification Search
CPC ............... A61F 2005/0132; A61F 2005/0165; A61F 2005/0167; A61F 5/0125; A61F 5/01; A61F 5/0123; A61F 2005/0158; A61F 2005/0172
See application file for complete search history.

(56) References Cited

U.S. PATENT DOCUMENTS

| | | |
|---|---|---|
| 2,172,484 A | 9/1939 | Tessier |
| 4,337,764 A | 7/1982 | Lerman |
| 4,381,768 A | 5/1983 | Erichsen et al. |
| 4,708,130 A | 11/1987 | Grudem |
| 4,768,500 A | 9/1988 | Mason et al. |
| 5,244,455 A | 9/1993 | Swicegood et al. |
| 5,256,135 A | 10/1993 | Avihod |
| 5,316,547 A | 5/1994 | Gildersleeve |
| 7,097,627 B2 | 8/2006 | Enzerink et al. |
| D529,180 S | 9/2006 | Ingimundarson et al. |
| D530,426 S | 10/2006 | Muehlenberend |
| D530,820 S | 10/2006 | Muehlenberend |
| D546,955 S | 7/2007 | Bauerfiend et al. |
| 7,597,674 B2 | 10/2009 | Hu et al. |
| D619,726 S | 7/2010 | Win |
| D623,760 S | 9/2010 | Chiang |
| 7,905,851 B1 | 3/2011 | Bledsoe |
| 8,021,317 B2 | 9/2011 | Arnold et al. |
| 2004/0068215 A1 | 4/2004 | Adelson et al. |
| 2005/0070831 A1* | 3/2005 | Cormier et al. ................ 602/26 |
| 2005/0148917 A1* | 7/2005 | Nathanson ..................... 602/23 |
| 2006/0155230 A1* | 7/2006 | Mason et al. .................. 602/16 |
| 2006/0247565 A1* | 11/2006 | Cormier et al. ................ 602/16 |
| 2007/0213648 A1 | 9/2007 | Ferrigolo et al. |

(Continued)

OTHER PUBLICATIONS

International Search Report and Written Opinion from corresponding PCT Application No. PCT/US2013/032951, May 29, 2013.

*Primary Examiner* — Victoria J Hicks
*Assistant Examiner* — Tarla Patel
(74) *Attorney, Agent, or Firm* — Workman Nydegger

(57) ABSTRACT

A hinge assembly for an orthopedic device having a pivoting assembly and a spring biased lock for locking the pivoting assembly in place. The hinge assembly also includes flexion and extension stop assemblies arranged for selectively locking onto notches formed along an arcuate channel located on an inner plate of the hinge assembly.

17 Claims, 9 Drawing Sheets

(56) References Cited

U.S. PATENT DOCUMENTS

2010/0256543 A1* 10/2010 McCune .................. 602/16
2011/0009786 A1* 1/2011 Chan ............................... 602/16
2011/0178448 A1 7/2011 Einarsson

* cited by examiner

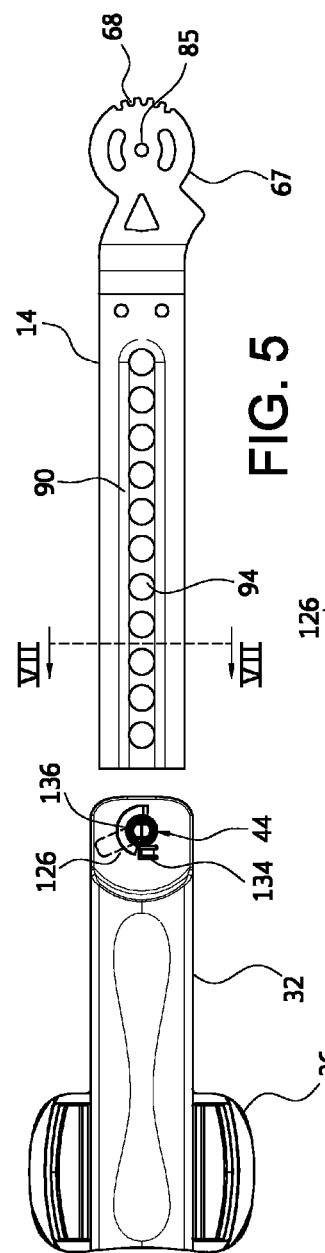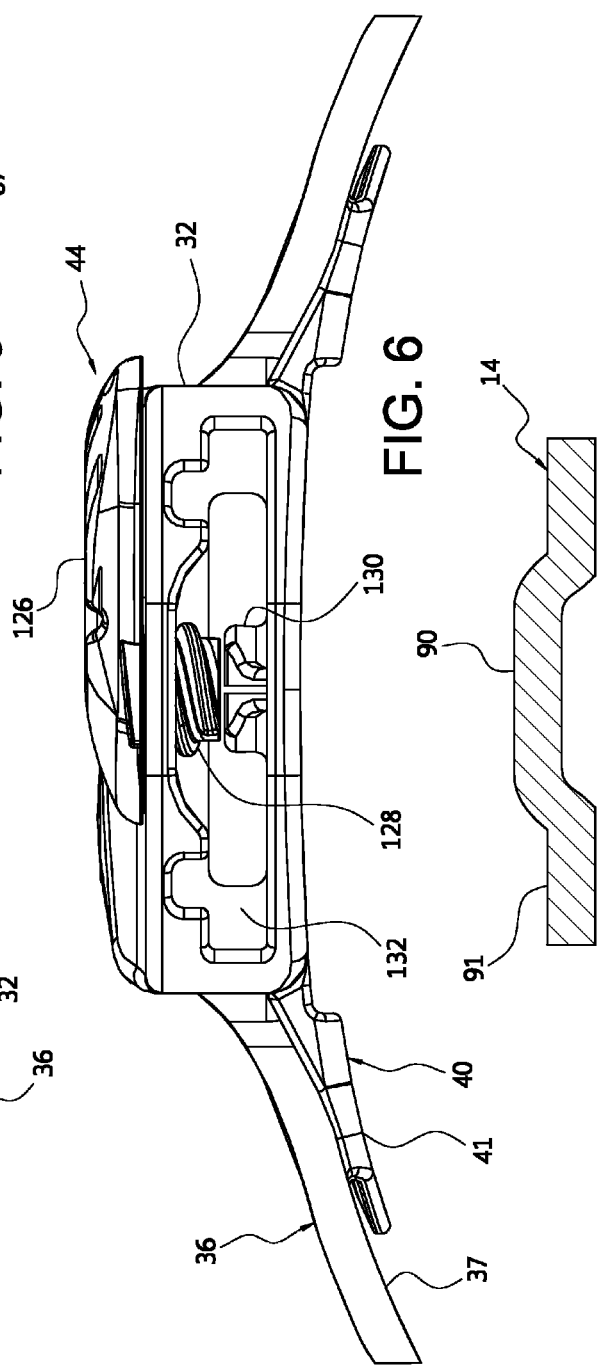

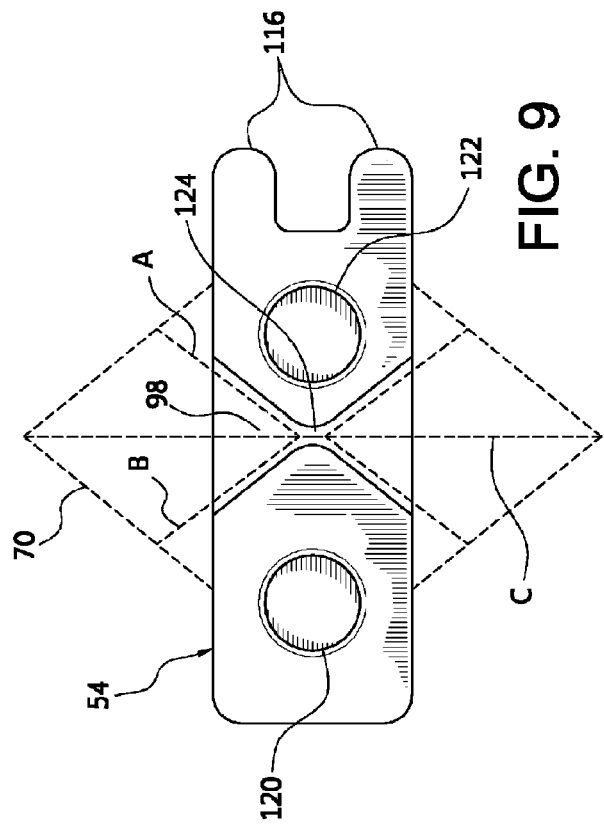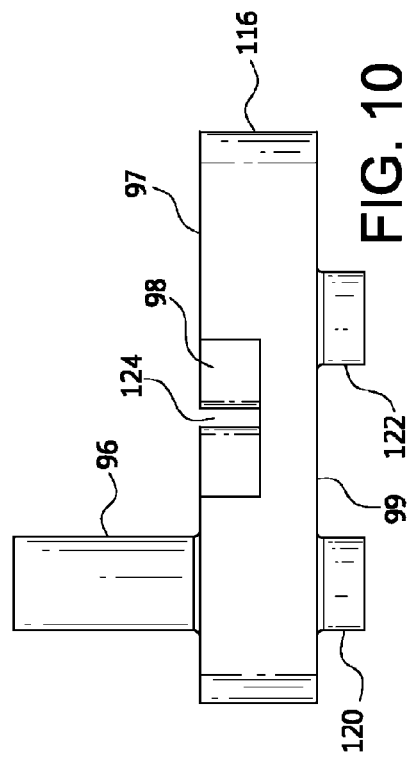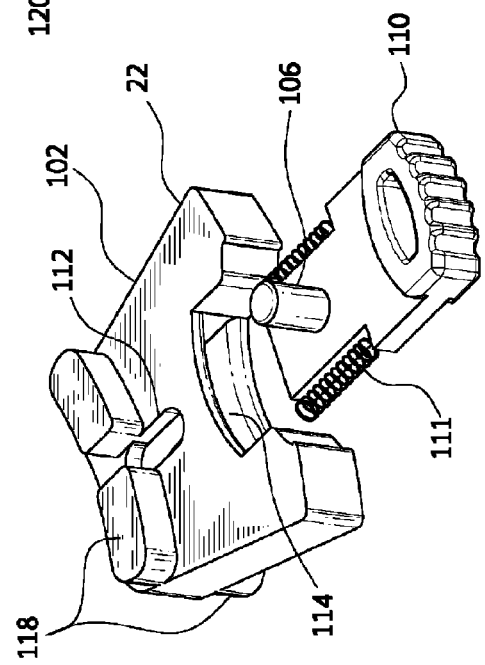

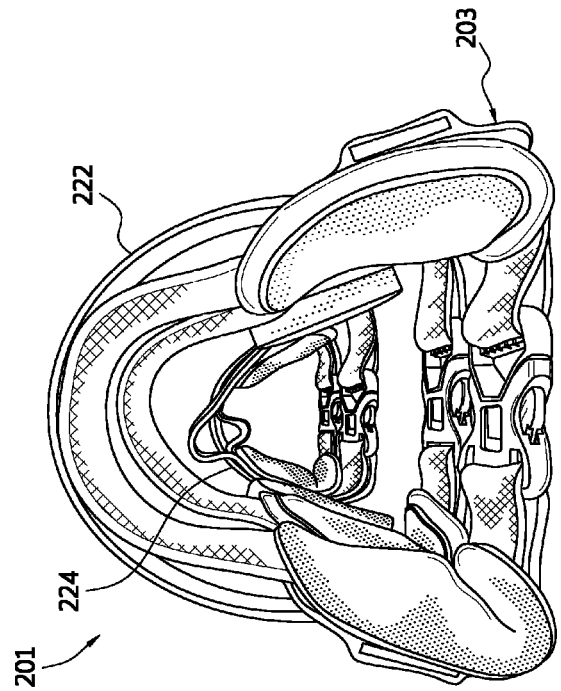
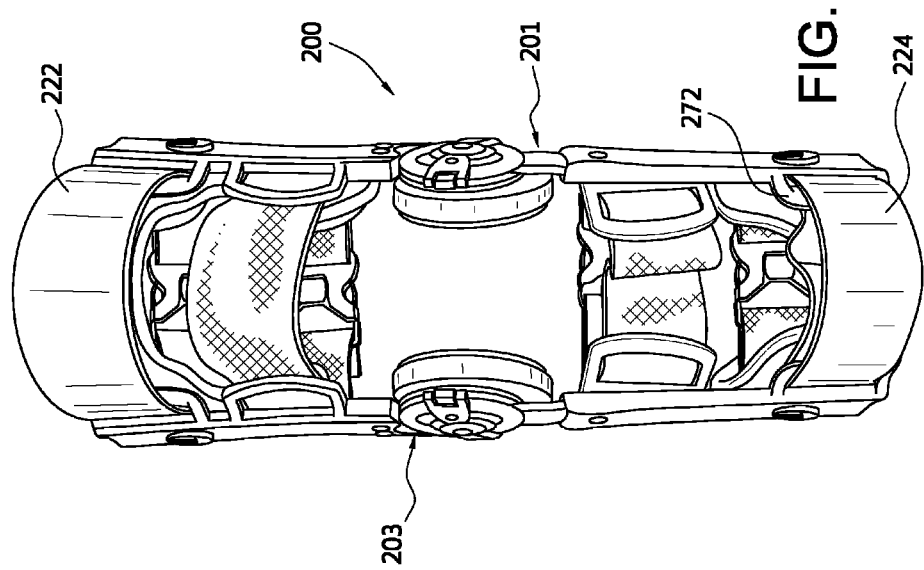

ORTHOPEDIC DEVICE

FIELD OF ART

The disclosure relates to orthopedic devices, and more specifically to adjustable and conforming post-operative knee braces.

BACKGROUND

In the field of orthopedic devices, and more particularly adjustable knee braces or supports, it is desirable that the brace include arrangements for limiting the movement of the lower leg relative to the upper leg both as to bending the knee or flexion, and as to extension of the lower leg relative to the upper leg. Various knee brace arrangements have been proposed, and these have included upper struts for extending along the thigh, and lower struts for extending along the lower leg or calf. These are normally provided both on the inside or medial side of the leg and also on the outer or lateral side of the leg; and the medial and lateral struts are normally padded, and provided with straps to hold them in place by circumferential tension. Pivoting arrangements are provided for coupling the upper and lower struts, and stops are provided for limiting both extension and flexion of the knee.

Many prior art knee braces have shortcomings, in that they are unduly bulky, or not simple to adjust, or secure to the leg without causing undue discomfort to the leg, or are otherwise not ergonomically configured.

In yet another drawback to prior art knee braces, particularly those used for post-operative rehabilitation, a challenge occurs when trying to don the brace over a surgically repaired knee. Because known prior art post-operative braces typically involve two strut arms on both sides of the knee, and these upright assemblies are merely connected to one another by flexible straps, the braces do not hold their shape or suspend horizontally to permit them to be applied quickly and easily with one hand. Often, at least one of the hands of the clinician must hold the leg upright and stabilize the knee when the brace is donned, with the other hand inserting the brace about the leg of the wearer.

Many prior art knee braces suffer from poor suspension means which fail to prevent the braces from migrating downwardly when worn by the wearer. The poor suspension is due in part to the shape of leg anatomy which is conical in nature and facilitates slippage of the brace. While strap systems are typically employed in the prior art, the straps do not typically fully touch or are adjacent to the entire leg anatomy over its circumference, and must be tightly tensioned to retain on the leg.

An orthopedic device for comfortably fitting to a wearer's limb, while providing easy adjustment of flexion and extension, and locking of the hinges, preventing migration of the device on the wearer's limb, and adjustment and initial sizing of the device is desired for those who fit and wear such orthopedic devices.

SUMMARY

The orthopedic device is described in the context of a post-operative knee brace adaptable to a variety of configurations and has various features. While described in this context, the various features may be adapted in other types of braces and supports other than the exemplary post-operative knee brace.

Certain features include buckles, strap arrangements, hinge and strut assemblies, brace expanders and other contributing features to minimize total fitting time and adjustment. Other features allow for minimization of migration on a wearer's limb or leg by providing an anti-migration strap and sticky or frictional foam on pads intended for placement adjacent the wearer's skin. The hinge assembly permits locking a leg in −10 degree extension with various flexion and extension stops indexed to this orientation. A pressure relief pad reduces pressure at a surgical site and minimizes risk in interfering with the surgical site. The orthopedic device is fitted a wide range of wearers with variable limb or leg length, width or shape with adjustable struts, and length and width adjustments.

The orthopedic device may include hinge assembly including a pivoting assembly defining a first opening, a first arm connected to the pivoting assembly and having a second opening with a shape corresponding at least in part and in location to the first opening, and a lock body slidably located within the second opening. The lock body defines a groove, and a spring is located within the groove and articulates between first and second positions of the lock body relative to the pivoting assembly.

The groove may define an hourglass configuration, and the spring articulates between opposed sides of the groove in the first and second positions. The groove defines a central narrow portion arranged to retain the spring therewithin.

The spring has an elongate, flat configuration in a neutral position between the first and second positions. The spring is flexed between the first and second positions corresponding to the locked and unlocked positions of the first arm relative to the pivoting assembly. The spring is biased about the central narrowed portion of the groove defining a fulcrum for flexing between the first and second positions while extending into and biased against walls of the second opening of the first arm.

A second arm may be rotatably connected to the pivoting assembly and have at least one notch. The lock body defines at least one locking tooth arranged to engage the at least one notch when the lock body is in the second position. The second arm defines a round head with a plurality of notches formed about the periphery thereof.

The lock body may define a button rod extending from a first surface and the pivoting assembly defines a slot arranged for accommodating the button rod in the first and second positions. The button is securable to the button rod outside of the pivoting assembly. The pivoting assembly may define an outer cover defining a plurality of indicia, and the lock button is arranged to lock at any one of the plurality of indicia.

The lock body may define at least one stabilizer extending from a second surface, and the pivoting assembly includes a first plate having at least one slot arranged for receiving the at least one stabilizer as the lock body moves between the first and second positions. According to a variation, the lock body defines a first stabilizer on a first side of the groove, and a second stabilizer on a second side of the groove.

The orthopedic device may include a pivoting assembly having flexion and extension stops. An embodiment of the pivoting assembly includes a first plate defining an arcuate channel and a plurality of notches oriented along the arcuate channel and directed toward an outer periphery of the first plate. A first stop assembly has a stop body and at least one stop flange located near an inner peripheral side of and protruding outwardly from a surface of the stop body. The stop flange is slidably received in the arcuate channel of the first plate.

The first stop assembly includes a spring biased button extending outwardly from the stop body and a stop pin coupled to the button. The stop pin is preferably biased toward an outer periphery of the stop body. In a first position, the stop pin is biased into and received in one of the plurality of notches thereby locking the position of the stop pin relative to the first plat. In a second position, the stop pin is biased to align with the at least one stop by depression of the button to rotate the first stop about the arcuate channel.

The pivoting assembly may include a first strut rigidly secured to an attachment end formed by the first plate, and a second strut rotatably coupled to the first plate and defining a first stop surface arranged to prevent rotation of the second strut relative to the first plate in a first rotational direction. The stop body is arranged to engage the stop surface. The pivoting assembly may also include a second stop assembly arranged to adjustably engage the arcuate channel. The second strut defines a second stop surface arranged to engage the second stop assembly, and is rotatable relative to the first plate between the first and second stop assemblies.

An embodiment of the orthopedic device includes first and second elongate struts each having a strap coupling member, and a flexible strap securing to the first and second struts by the strap coupling members. A semi-rigid and resiliently bendable expander is connected to and spans a predetermined length between the struts. The expander provides two main configurations for the orthopedic device including maintaining the first and second struts in a flat configuration relative to one another and a curved configuration upon application of a load on the first and second struts. The expander reverts to a flat configuration upon removal of a load or from the first and second struts.

A method for donning an orthopedic device includes usage of the brace expander. The method includes the step of connecting a semi-rigid and resiliently bendable expander connected to the struts and spanning a predetermined length between so the device has a substantially flat configuration; placing the orthopedic device under a wearer's limb while the orthopedic device is in the flat configuration by the expander; and conforming the orthopedic device about the wearer's limb by applying a load to and bending the brace expander into a curved configuration.

The orthopedic device may include cuff and strut assemblies providing for easy adjustment in the length of these assemblies to accommodate the specific anatomy of a wearer of the orthopedic device. These assemblies may include malleable components that may correspond to the tibial and femoral regions of the wearer's leg. Despite the malleability, the cuff and strut assemblies remain rigid when worn and are arranged to provide saggital and coronal plane stabilization. This enables fixation of the knee flexion or extension, and fixes the position of the knee mediolaterally for pain relief.

The numerous advantages, features and functions of the embodiments of the orthopedic device will become readily apparent and better understood in view of the following description and accompanying drawings. The following description is not intended to limit the scope of the orthopedic device, but instead merely provides exemplary embodiments for ease of understanding.

BRIEF DESCRIPTION OF THE DRAWINGS

FIG. 5 is a perspective plan view of the lower strut and lower cuff assembly of FIG. 1 showing the lower cuff assembly removed from the lower strut.

FIG. 6 is an elevational view showing the lower cuff assembly in FIG. 5.

FIG. 7 is a cross-sectional view of the lower strut taken along line VII-VII in FIG. 5.

FIG. 8 is an exploded view of a stop assembly in the upright assembly of FIG. 1.

FIG. 9 is a plan view of the lock base of FIG. 2.

FIG. 10 is an elevational view of the lock base of FIG. 9.

FIG. 13 is an elevational view showing the post-operative brace of FIG. 11 in a closed-curved configuration.

FIG. 14 is a plan view showing the post-operative brace of FIG. 11 in a closed-curved configuration.

Figure 4:
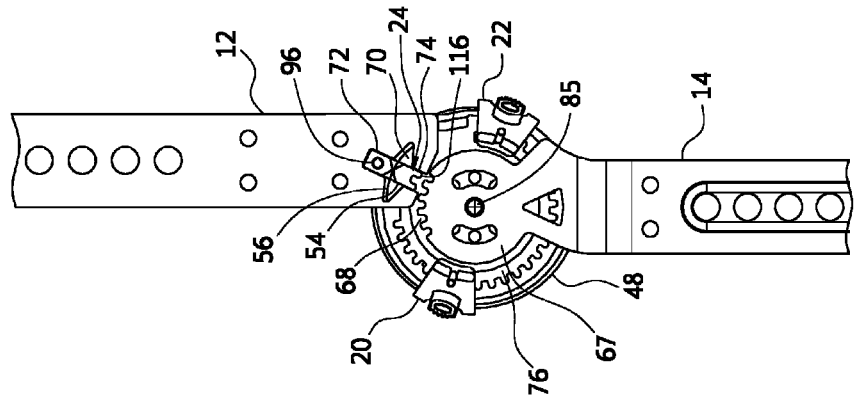
FIG. 4 is a partial elevational view of the upright assembly of FIG. 1 without an outer plate provided thereon.
Figure 3:
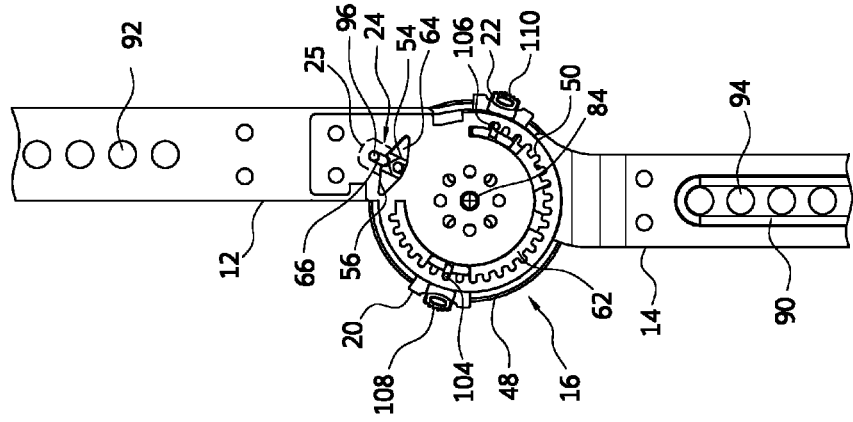
FIG. 3 is a partial elevational view of the upright assembly of FIG. 1 without an outer cover provided thereon.

In the various figures, similar elements are provided with similar reference numbers. The drawing figures are not drawn to scale, or proportion, but instead are drawn to provide a better understanding of the components, and are not intended to be limiting in scope, but rather provide exemplary illustrations.

DETAILED DESCRIPTION OF VARIOUS EMBODIMENTS

For further ease of understanding the exemplary embodiments of an orthopedic device in the form of a post-operative knee brace as disclosed, a description of a few terms is necessary. As used, the term "upper" has its ordinary meaning and refers to a location that is top or above a median portion (such as in a pivoting assembly proximate to the knee). Likewise, the term "lower" has its ordinary meaning and refers to a location below a median portion (such as in a pivoting assembly proximate to the knee) and is in contrast to the term "upper."

The terms "inner" or "inside" also has the ordinary meaning and refer to an inside portion or location adjacent to or more proximate to a leg or knee. The terms "outer" or "outside" have their ordinary meaning and refer to a relative location opposite an inner or inside portion, and is the side or surface typically on the outside of or proximate to the outside of the device.

The terms "medial" and "lateral" are relative terms generally understood as indicating location near the midsaggital plane or midline. Therefore, elements located near the midline are "medial" and those elements that are further from the midline are considered to be "lateral." The term "central" is used to denote the area along the midline of a joint dividing and sharing regions of the medial and lateral regions.

The terms "rigid," "flexible," and "resilient" may be used to distinguish characteristics of portions of certain features of the orthopedic brace. The term "rigid" should denote that an element of the device is generally devoid of flexibility. Within the context of support members that are "rigid," it is intended to indicate that they do not lose their overall shape when force is applied, and in fact they may break if bent with sufficient force. The term "flexible" should denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to connote properties that may have some degree of flexibility or resiliency.

In referring to the orthopedic device in the exemplary form of a post-operative knee brace in FIGS. 1-10, an upright assembly 10 (either for a lateral or medial side of the leg in the knee brace) is shown having upper and lower struts 12, 14 linked to one another by a pivot assembly 16. These struts are sometimes referenced as femoral struts (as extending along the femur or upper leg bone) and tibial struts (extending along the tibia, or the principal lower leg bone). An upright assembly on the other side of the knee is also provided with struts extending up and down the leg, but these are not visible in FIG. 1. The struts 12, 14 are preferably constructed from a malleable material to better conform to the shape of the wearer's leg.

The pivot assembly 16 permits rotation of the upper and lower struts 12, 14 relative to one another about a central axis 18 denoted by a central fastener. The pivot assembly 16 includes first and second pivot stop assemblies 20, 22 biased to prevent extension and flexion of the knee of the wearer of the knee brace.

Indicia 26 are on the pivot assembly 16 to allow a wearer to quantify where to set a prescribed range for extension and flexion of the knee. For a post-operative wearer, it is desirable to limit the bending of the knee both in the extension direction when the wearer is straightening his or her leg, and in the flexion direction where the wearer is bending the leg at the knee as far as practical under the circumstances. The indicia may represent various angles of extension and flexion.

The pivot assembly 16 also includes a drop lock 24 that can quickly and easily lock down the relative pivoting motions of the upper and lower struts 12, 14. A sliding drop lock button 25 is preferably on the pivot assembly 16 so that when slid into its locking position in a recess 58 formed along the outer cover 46 of the pivoting assembly 16, the drop lock 24 interlocks the upper and lower struts 12, 14 to inhibit their pivoting action. Indicia 28 are provided allowing the wearer to know at what angle the pivot assembly should be locked. A preferable range is −10 to 40 degrees.

The drop lock 24 may be actuated to lock the knee in flexion at −10 degrees. This setting is advantageous in that it permits hyperextension of the knee, and affords the clinician to determine the proper extension position for the wearer. It has been found that some knees hyperextend naturally, which a −10 degrees setting is properly maintained.

An upper cuff assembly 30 is adjustably mounted along the length of the upper strut 12 and lockable to the upper strut 12 by an upper cuff lock device 42 along adjustment holes 92. The upper cuff assembly 30 has an integrally formed upper strap coupling member 34, and the upper strut 12 may likewise carry a detachable upper strap coupling member 38. Both the strap coupling members 34, 38 are adapted to carry and support a strap feedable therethrough and lockable therewith. A lower cuff assembly 32 likewise adjustably secures along the length of the lower strut 14, and is lockable in place by a lower cuff lock device 44 along adjustment holes 94. An integrally formed lower strap coupling member 36 and a detachable lower strap coupling member 40 are also provided in combination with the lower strut 14 and the lower cuff assembly 32.

The cuff assemblies and the strap coupling members may be contoured to accommodate the shape of a leg. The strap coupling member may comprise D-rings that can be mounted, fastened, molded, or glued to either the cuff assemblies 30, 32 or the struts 12, 14.

Figure 1:
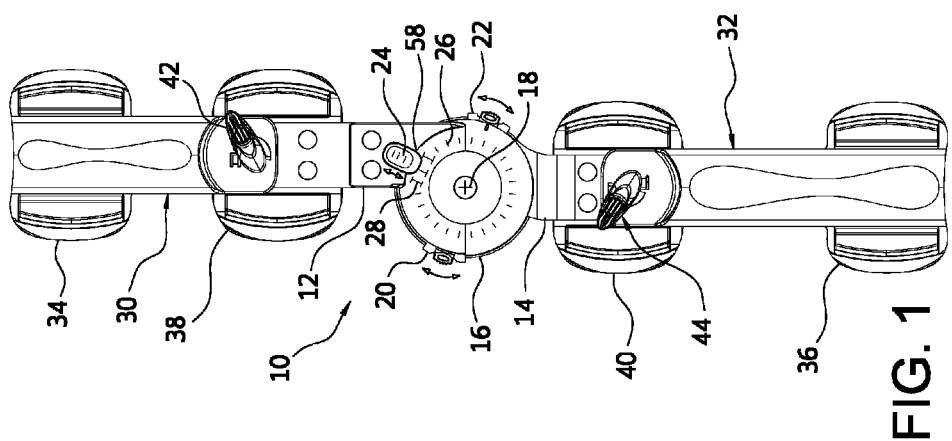
FIG. 1 is an elevational view of an upright assembly of an orthopedic device in the form of a post-operative brace.

In the exemplary embodiment in FIG. 1, the upper strap coupling member 34 is at the end of the upper strut 12, and likewise the lower strap coupling member 36 is at the end of the lower strut 14, whereas the detachable upper and lower strap coupling members 38, 40 are secured directly to the struts 12, 14. Adjustable straps (not shown) with hook and loop fasteners, buckles can then be looped through the strap coupling members. The straps are used to attach the knee brace to the wearer's leg. The large surface area and contour of the cuffs and strap coupling members (see surfaces 37, 41 in FIG. 6) help with fitment of the knee brace to the wearer's leg and minimizes shifting of the leg within the knee brace.

FIGS. 5-7 show the lower strut 14 and an exemplary lower cuff assembly 32 is useable for either the upper or lower struts in that the lower cuff assembly can likewise be used on the upper strut 30. The lower strut 14 defines a strut head 67 having a plurality of notches 68 formed about a portion of the periphery for engagement with the drop lock 24. The lower strut 14 is elongate beyond the strut head 67 and defines a profile having a raised ribbed section 90 forming the plurality of adjustment holes 94 and a lower, flat portion 91 surrounding the ribbed section 94. The lower cuff assembly 32 defines a contoured slot 132 arranged to receive the strut 14. The ribbed section 90 improves the strength of the strut 14, and allows for better fitting within the cuff assembly by preventing shifting within the contoured slot 132.

The lower cuff lock device 44 is depicted in FIG. 6, and includes a screw-in lever 126 secured to a threaded post 128 which is rotatable relative to the lower cuff assembly 32 along a ramped surface 136 terminating with a stop 134. The threaded post 128 engages corresponding threads (not shown) formed by the lower cuff assembly 32, and is adapted to extend through a selected adjustment hole 94 of the lower strut 14. A detent 130 is provided at the base of an interior surface of the lower cuff assembly 32 preventing further travel of the threaded post and securing the lower strut 14 to the lower cuff assembly 32.

To prevent the wearer from accidentally overly twisting the screw-in lever 126, the optional turn stop 134 positioned on the surface of the lower cuff assembly 32 blocks the outer limit of rotational travel of the screw-in lever 126. The ramped surface 136 has a ramp-like, flat engagement face designed to engage the rotating screw-in lever 126. The screw-in lever 126 can be rotated clockwise through about 180 degrees of travel until encountering the rising resistance of moving up the ramp of the turn stop 134, and the screw-in lever 126 can be rotated about 180 degrees counterclockwise until it encounters the flat engagement face at the opposite side of the turn stop 134.

The pitch of the threads for the post 128 is selected so about 180 degrees clockwise turn is sufficient to fully engage the post 128 with the adjustment hole 94. Smaller or larger angular turns of the screw-in lever 122 to lock and unlock the components are contemplated. The preferred 180 degrees rotational range to lock/unlock the screw-in lever 126 is selected for ergonomics and ease of use for the knee brace wearer.

To provide sufficient strength, the screw-in lever 126 and cuff assemblies 30, 32 are preferably made from glass filled nylon or like polymers. The cuff assemblies may have an aluminum, steel, or like metal skeleton over which the plastic is molded if more strength is desired.

Because the adjustment holes 92, 94 of the struts are covered by the cuff assemblies 30, 32 when the two parts are assembled, the clinician or wearer cannot easily align the post 128 with the desired adjustment hole 92, 94 to interlock the cuff assembly and strut together. To enhance easy alignment of the post 128 and adjustment holes 94, a detent 130 is provided at the base of an interior surface of the lower cuff assembly 32 preventing further travel of the threaded post and securing the lower strut 14 to the lower cuff assembly 32.

Therefore, as each adjustment hole 94 slides past the detent 130, noticeable click-stop can be felt and heard by the user indicating that the post 128 and one of the adjustment holes 94 are aligned. In the preferred embodiment, the detent 130 is a bump, ridge, ramp, or like click-stop that slightly enters and easily slides out of any of the adjustment holes 94 of the strut 14.

Figure 2:
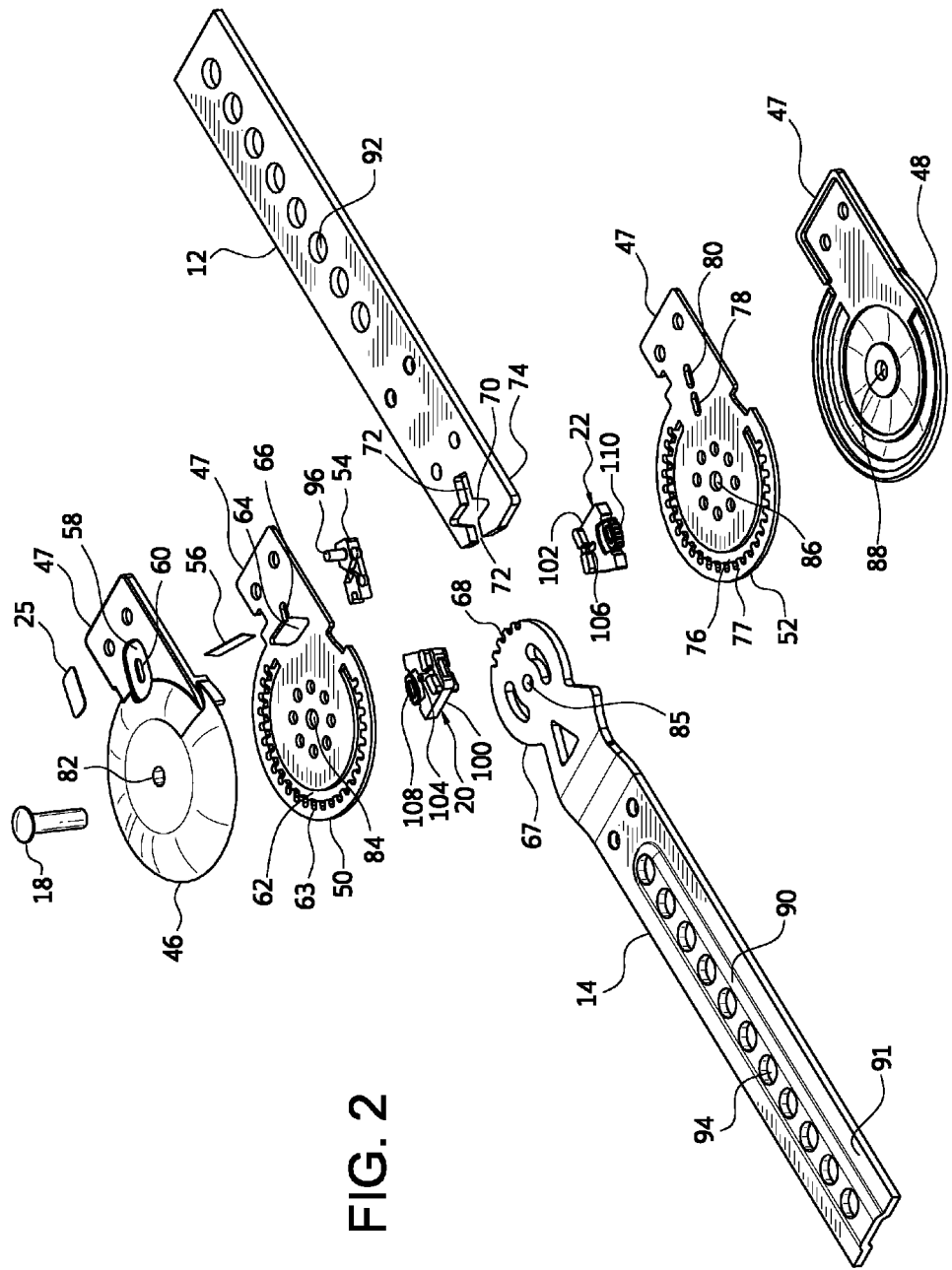
FIG. 2 is an exploded view of the upright assembly of FIG. 1.

As depicted in FIG. 2, the pivot assembly 16 includes an outer cover 46, an outer plate 50, a strut head 67 belonging to the lower strut 14, an inner plate 52, and an inner cover 48, all of which rotate about a central axis denoted by a central fastener 18. The outer cover 46, outer plate 50, strut head 67, inner plate 52, and inner cover 48 each have central holes 82, 84, 85, 86, 88, respectively, through which the central fastener 18 extends. The outer and inner plates 50, 52 secure to the upper strut 12 via fasteners, such that the outer and inner plates 50, 52 rigidly secure to the upper strut 12, wherein the lower strut 14 rotates relative to the outer and inner plates 50, 52.

The first and second pivot stop assemblies 20, 22 are rotatable relative to the outer and inner plates 50, 52, about arcuate channels 62, 76 formed respectively by the inner and outer plates. A plurality of notches 63, 77 are defined along the arcuate channels 62, 76, into which the pivot stop assemblies 20, 22 selectively engage to delimit extension and flexion of the pivot assembly 16.

As shown in FIG. 8, an exemplary embodiment of the second stop assembly 22 includes a stop body 102, and button member 110 that slidably inserts into an opening 114 formed by the stop body 102. The outermost surfaces of the button member 110 is preferably knurled, ribbed or textured for non-slip engagement. The button member 110 is spring-biased by springs 111 against the stop body 102 and which are located on opposed sides of the button member 110. A pin 106 extends from opposed upper and lower surfaces of the button member 110 and protrudes from slots 112 formed by opposed sides of the stop body 102. The pin 106 is adapted to extend into the notches 63, 77 of the outer and inner plates 50, 52. Stop flanges 118 protrude from upper and lower surfaces of the stop body 102, and are configured to be received with the arcuate channels 62, 76 of the outer and inner plates 50, 52 so as to permit stable rotation and securement of the stop assemblies relative to the outer and inner plates 50, 52.

The first stop assembly 20 likewise has a stop body 100, a corresponding stop pin 104 and stop button 108, and is otherwise identically configured as the second stop assembly 22.

In operation, the pin 106 which moves inward with the push button 110 to change settings whereby the second stop assembly 22 can rotate about the arcuate channels of the outer and inner plates, but is spring biased outward to engage one of the notches 63, 77 once the button is released with the stop flanges 118 located within the arcuate channels 62, 76. Similarly, the locking pin associated with push button locks the stop by engagement with a selected one of the notches about the arcuate channel.

The drop lock 24 includes a lock base 54 and a cooperating spring 56 which slidably engages the pivot assembly 16 and is configurable between locked and unlocked positions. As shown in FIG. 9, the lock base 54 defines a groove 98 on an outer surface of the lock base 54, and the groove forms an hourglass configuration with a central narrowed portion 124 for retaining the spring 56. The hourglass groove 98 permits the flat spring 56 to flex between two positions corresponding to the locked and unlocked positions in which the spring is biased about the narrowed portion 124 which serves as a fulcrum for flexing between the positions while extending into and biased against walls of the upper strut spring opening 70.

At a forward end, the lock base 54 defines locking teeth 116 adapted to selectively engage the notches 68 on the strut head 67. The lock base 54 defines a button rod 96 which extends from an outer surface 97 of the lock base 56 and is located near the rear end of the lock base 54. The button 25 engages a top portion of the button rod 96 which protrudes from the outer cover 46.

First and second stabilizers 120, 122 protrude from an inner surface 99 of the lock base 54, and preferably take the form of short cylinders. The first and second stabilizers 120, 122 are generally centrally located along the length of the lock base 54. The first stabilizer 120 is preferably coaxial with the button rod 96, and the second stabilizer 122 is located inwardly from and beyond the locking teeth 116, and a distance from the forward end of the lock base 54 so as not to interfere with the locking teeth 116 when they engage the notches 68. The locking teeth 116 do not protrude outwardly from the lock base 54 beyond either the outer and inner surfaces 97, 99 so they do not interfere with the outer and inner plates 50, 52.

The button rod 96 slidably engages a slot 60 formed by the outer plate 46, and is at an attachment end 47 of the outer plate 46 adapted for securing onto an end portion 71 of the upper strut 12. Each of the inner plate and inner and outer covers likewise have a corresponding attachment end. The outer plate 50 defines an opening 64 forming a diamond shape, and a slot 66 depending from the opening 64 and in alignment with and corresponding in shape to the slot 60.

The end portion 74 of the upper strut 12 has an opening 70 aligned with and corresponding to the shape of the opening 64 of the outer plate 50, and a slot 72 arranged on opposed sides of the opening 70 with the same width of the lock base 54 to permit sliding of the lock base 54. The spring 56 is adapted to at least flex in the diamond opening 70 between locked and unlocked positions. The inner plate 52 defines first and second lock slots 78, 80 in which the first and second stabilizers 120, 122 slide within.

As illustrated in FIG. 9, in operation, when the drop lock is unlocked, the button is pressed toward the upper strut 12, wherein the spring 56 in position A flips direction to bias the lock base 54 away from the notches 68 on the lower strut head 67. When in the locked position B, the spring 56 deflects and flips in an opposed direction maintaining the locking teeth 116 engaging the notches 68. When at the position C of inflection, the spring 56 is essentially flat and generally spans the width of the opening 70. The button rod and the stabilizers slide through the appropriate slots to provide stability to the lock base.

Turning to the embodiment of FIGS. 11-14, the post-operative brace 200 is configured with brace expanders that overcome the donning challenge that occurs when a clinician tries to fit the brace 200 onto a wearer. From this embodiment, the brace may be formed as a semi-rigid unit that can easily be managed with a single hand whereas the other free hand can hold the leg to position the brace.

Figure 11:
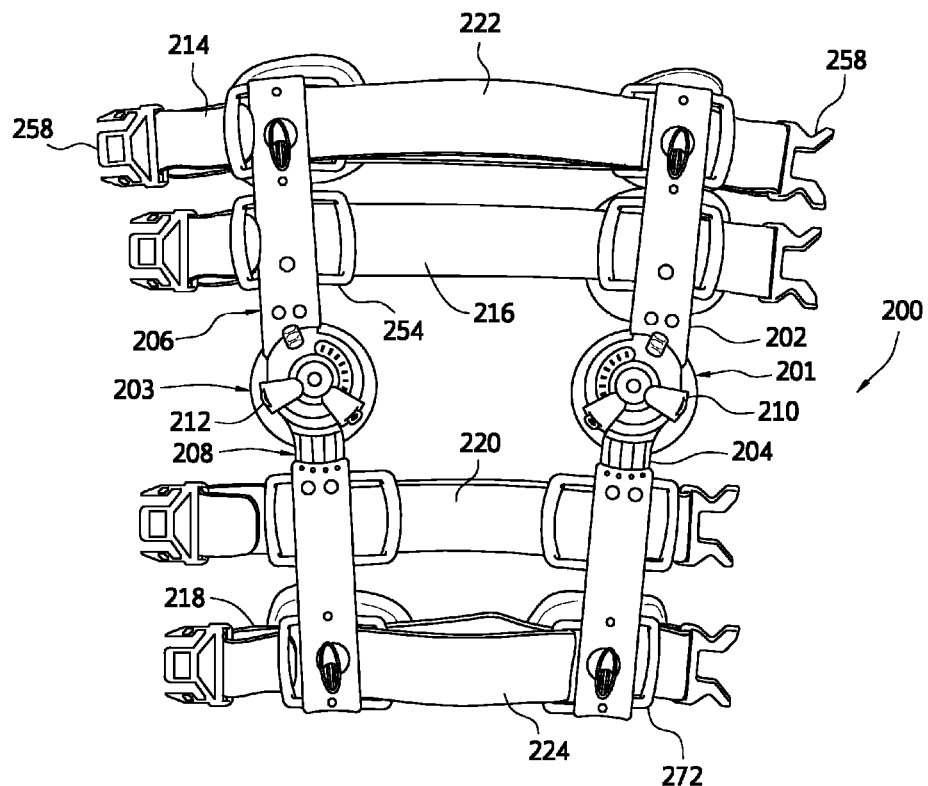
FIG. 11 is an elevational view of an outer side of a post-operative brace in an open-flat configuration.

Particularly, as depicted in FIG. 11 in the open-flat configuration showing the outside of the brace, the brace 200 includes first and second side upright assemblies 201, 203, similar to those for FIGS. 1-10. Each of the upright assemblies 201, 203 has upper struts 202, 206, respectively, and lower struts 204, 208, respectively, and are connected to one another by corresponding pivot assemblies 210, 212. First and second upper strap assemblies 214, 216 connect to the upper struts 202, 206, and first and second lower strap assemblies 218, 220 connect to the lower struts 204, 208. The straps each carry corresponding fasteners 258, such as buckle parts, which secure to one another to convert each of the strap assemblies to a circumferential strap, for securing about the leg of the wearer.

The straps may be textile-based and lack rigidity in that they cannot maintain the struts in a relative position without support. The straps are preferably flexible, but lack resiliency in that once adjusted, they require additional movement to return them to their original orientation.

According to this embodiment, a rigid or semi-rigid brace expander 222 is positioned between the upper struts 202, 206, and a rigid or semi-rigid brace expander 224 positioned between the lower struts 204, 208. The brace expanders 222, 224 generally run parallel to the corresponding first upper and lower strap assemblies 214, 218, respectively.

The brace expanders 222, 224 have two main configurations: a flat configuration in which they maintain the first upper and lower strap assemblies 214, 218 in a substantially flat configuration, and a curved configuration which corresponds to the wearer's leg. The brace expanders 222, 224 may be adjusted relative to the upper and lower struts by suitable fasteners or be received by the strap coupling members (i.e., 272), effectively by lengthening or shortening the distance between the upright assemblies 201, 203. The brace can be provided with only a single brace expander, either corresponding to the upper leg or lower leg of the wearer, or include multiple brace expanders along the length of the struts.

Once the brace is installed on the leg of the wearer, the brace expanders may be removed. Suitable fasteners may be secured to the brace expanders and the upright assemblies to permit removal after the knee brace has been initially donned on the wearer. The brace expanders can also be trimmed to length prior to donning the brace on the wearer during the initial fitment of the brace to accommodate the circumference of the wearer's leg. However, if the brace expanders remain on the brace even after the brace is donned, they may increase pressure exerted on the leg, thereby increasing the sagittal plane support of the knee against flexion.

Figure 12:
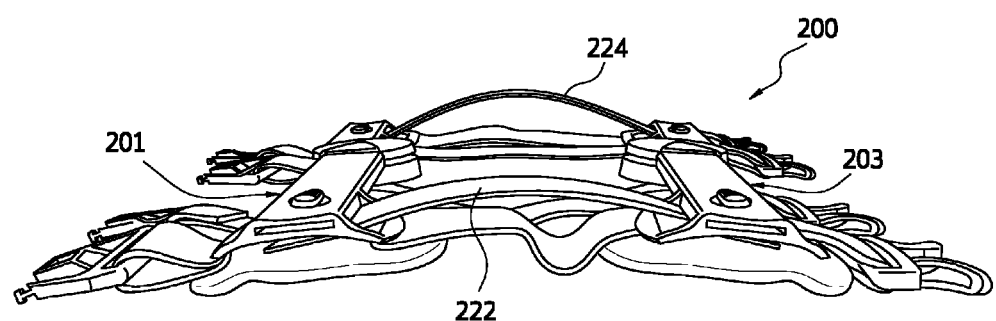
FIG. 12 is a plan view showing the post-operative brace of FIG. 11 in the open-flat configuration.

As shown in FIG. 12, the brace 200 is in the open-flat configuration wherein the brace expanders 222, 224 are generally flat in that the expanders may bow outwardly slightly depending on their sizing before the brace is fitting for an actual wearer. According to FIGS. 13 and 14, the brace 200 is in the closed-curved configuration, particularly with the brace expanders 222, 224 curved. The brace expanders are generally bistable in that they either posses a flat configuration or upon a force, they bend into a curved configuration.

The brace expanders are preferably constructed from a sheet type material that has shape memory and resiliency such that if bent from an initial flat configuration, the brace expander returns to the initial flat configuration once the load is released. An exemplary material is a thermoplastic sheet substantially rigid to sustain a flat configuration when supporting opposed upright assemblies on either side of the sheet. This exemplary material is provided by Kydex, LLC under the name KYDEX 100.

Figure 15:
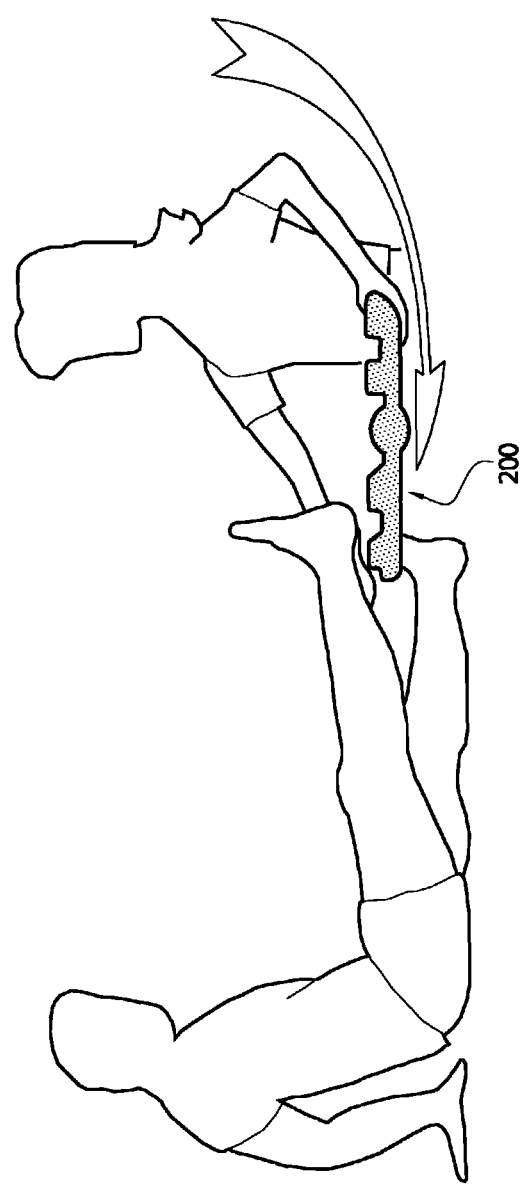
FIG. 15 is a schematic view showing the donning of the post-operative brace onto the leg of a wearer by a clinician.

FIG. 15 schematically depicts the donning of the brace 200 by a clinician onto the leg of the wearer. The brace 200 is in the open-flat configuration and held by one hand by the clinician, whereas this frees the other clinician's hand to orient and position the leg of the wearer. The brace expanders maintain the upright assemblies in a predetermined, stable configuration with suitable spacing as considered necessary for a wearer when the brace is donned onto the wearer.

Figure 16:
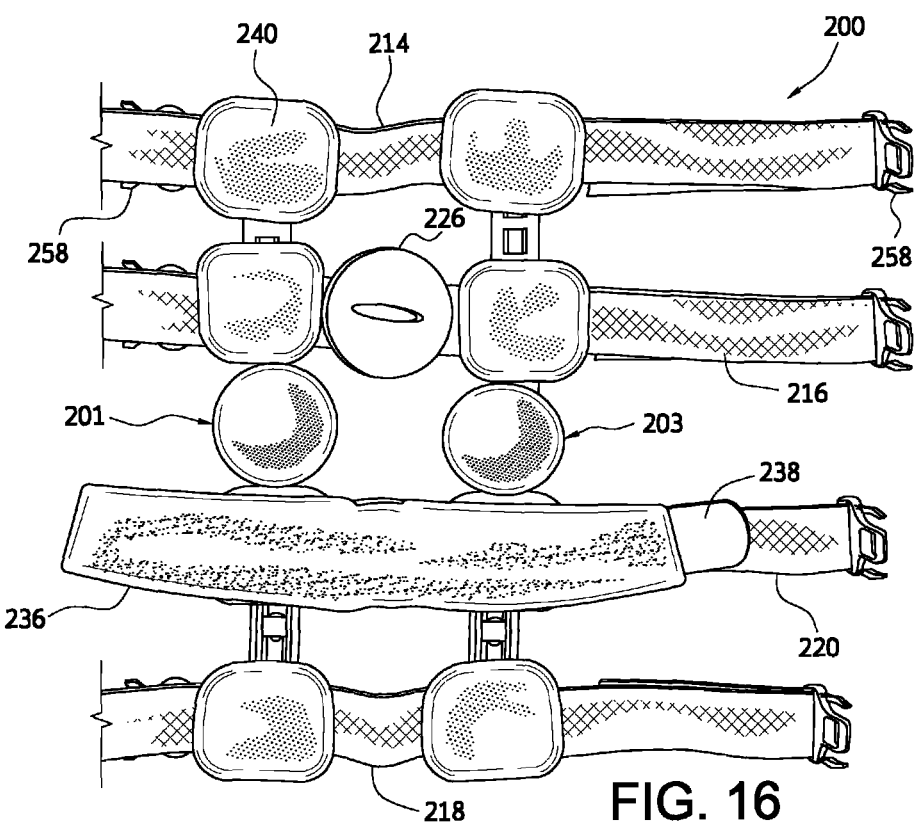
FIG. 16 is a plan view showing an inner side of the post-operative brace in FIG. 11.

Turning to FIG. 16, the inside of the brace 200 is in the open-flat configuration. A pressure relief pad 226 is on the second upper strap assembly 216 which is provided with hook receivable or unbroken loop material. The pressure relief pad 226 can be located along any of the strap assemblies, and is not limited to the location depicted.

Figure 17:
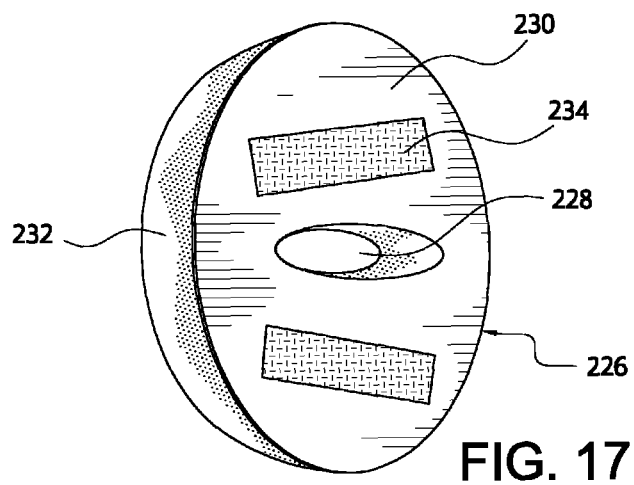
FIG. 17 is a perspective view showing a pressure relief pad used in the post-operative brace of FIG. 16.

FIG. 17 depicts the pressure relief pad 226 as having a central opening 228 intended to be placed over a wearer's incision following surgery. The pressure relief pad 226 has a backing layer 230, formed from an exemplary material such as a hook-receivable or unbroken loop material, and a foam core 232 which has a surface intended to be adjacent the leg of the wearer. Suitable fastening strips 234 are located along the backing layer 230 for engagement to the strap assemblies.

While it is preferred that the central opening has an elongate oval shape, as illustrated, the central opening is may take on a variety of shapes and forms, and is not limited to the illustrated configuration. The pressure relief pad shape itself may take on many forms, to accommodate incision sites of a wearer of the brace, and a plurality of pressure relief pads may be employed with the brace and used at different times during the healing process of the brace wearer.

The pressure relief pad is an optional feature arranged to be placed over an incision site to reduce pressure directly on the incision. The opening of the pad should be located over the incision site to minimize or completely distribute pressure around the incision site but not over the incision site. In this manner, loads exerted on the leg by the strap assemblies do not interfere with the healing of the incision site, and reduce or avoid causing discomfort to the wearer that may otherwise occur without the pressure relief pad. In an example, the pressure relief pad may be placed at the tibial tubercle where the surgeon drills the tibial hole to attach the distal portion of the ACL ligament.

The brace 200 also includes an anti-migration wrap 236 located along any of the strap assemblies, and is particularly shown as located along and generally parallel with the second lower strap assembly 220. The anti-migration wrap 236 includes an attachment element 238 located at a first end, and which secures to a second end of the wrap to effectively wrap about the circumference of the leg of the wearer in supplement to or combination with the corresponding strap assembly.

Figure 18:
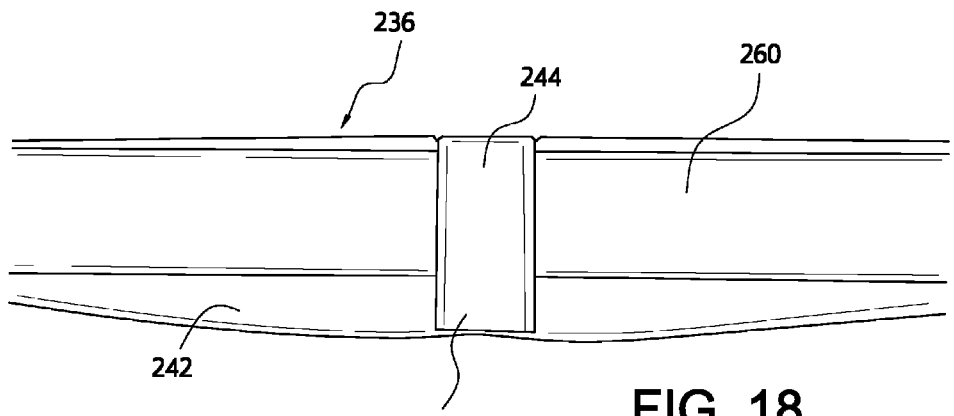
FIG. 18 is a plan view showing an anti-migration wrap in the post-operative brace of FIG. 16.

According to the variation in FIG. 18, the anti-migration wrap 236 may secure to the strap assembly by a strap keeper 244 that provides a channel for the strap assembly to extend through, with an end having a fastener 246 that secures to a surface 242 of the anti-migration wrap. The fastener 246 may have hook material and the surface 242 may be formed from an unbroken loop material permitting installation of the fastener directly to the surface of the wrap. This permits selective placement of the wrap along the length of a corresponding strap assembly, and likewise lets the wrap slide along the strap if the fastener is not tightly secured to the width of the strap assembly. Alternatively, the fastener may be a button and a corresponding button element may be provided on the surface 242 of the wrap which can be set to either permit sliding of the wrap along the strap assembly or tightly securing to the belt assembly to inhibit sliding. Likewise, means can be provided to secure the wrap directly to a strap assembly by suitable fastener means.

The anti-migration wrap 236 preferably has geometry broader than the strap belonging to the strap assembly. The geometry allows the anti-migration wrap to cover a broader portion of the leg geometry than a corresponding strap assembly, thereby urging generally uniform pressure about the entire circumference of the wearer's leg. Preferably, the anti-migration wrap is located below the knee and just above the apex of the calf muscle to capture a smaller proximal circumference of the calf which reduces distal migration.

The anti-migration wrap can be formed from a variety of materials. In a preferred embodiment, the anti-migration wrap is flexible and breathable. According to different variations, the wrap may stretch or minimally stretch when secured about the leg of the wearer. The wrap may comprise a foam material having substantially high frictional properties. According to this variation, the anti-migration wrap is not intended to be constricting but rather have high frictional properties to prevent migration. The anti-migration wrap may be formed from other materials as well such as with a fabric having sections coated with silicone or another polymer having enhanced frictional properties.

Figure 19:
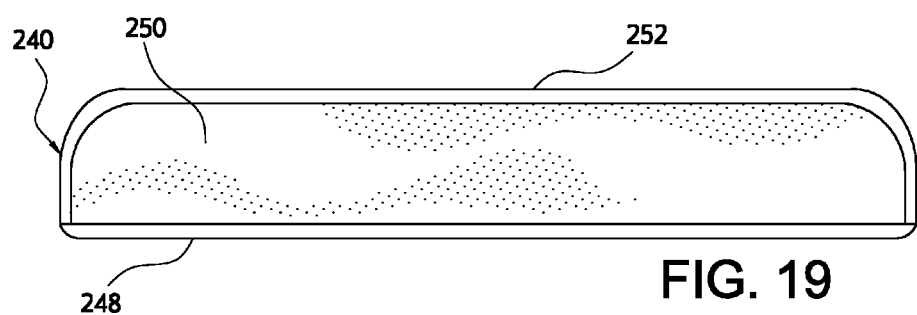
FIG. 19 is a cross-sectional view showing a friction pad in the post-operative brace of FIG. 16.

The brace 200 may include friction pads 240 that have a surface with high frictional properties. In referring to FIG. 19, the friction pad 240 has a surface formed from a "sticky" frictional foam layer 248 having a high frictional value and is intended to face or lay adjacent to the wearer. The frictional foam layer is in contrast to a core 250 of the friction pad which is formed from a non-clickable foam. The frictional foam layer has a frictional value at least 2 times more frictional than the non-clickable foam. A non-clickable foam is considered to be foam that has a superior resiliency so its edges spring back and do not stay compressed after it is die cut and after pressure is released from the foam, such as after when the knee brace is doffed. A layer of hook receivable material 252 may apply to exterior surfaces outside the frictional foam layer.

According to a variation, the frictional foam layer has a thickness substantially less than the core foam. In this variation, the frictional foam layer has a thickness in the range of 1.0 to 3.0 mm, and the core has a thickness in the range of 10.0 to 20.0 mm. Preferably, the frictional foam layer and the core foam are polyester polyurethane foams, with the frictional foam layer having a density in the range of about 20-40 $kg/m^3$, more preferably 27 $kg/m^3$ at a thickness of about 2 mm, and the core foam has a density in the range of about 50 $kg/m^3$ to 65 $kg/m^3$, and more preferably 57 $kg/m^3$ at a thickness of about 11 mm. The compression force for 25% deflection of the frictional layer may be within the range of 2.8 $kN/m^2$–3.4 $kN/m^2$ (at a thickness of about 2 mm), and the core foam may be within the range of 4.0 $kN/m^2$–5.0 $kN/m^2$ (at a thickness of about 11 mm).

The friction pad may be constructed without the core foam such that the frictional layer takes on a thicker thickness, such as 10-14 mm, and a hook receivable material covers at least a surface of the frictional layer. The anti-migration wrap may have the same general construction as the friction pads, such as in the three layer friction pad discussed above.

The friction pads 240 having the frictional foam layer are preferably tacky, and should cover various the various strap coupling members and other components of the brace. Because the friction pads are tacky or sticky, they assist in reducing migration of the brace over the leg of the wearer. The anti-migration wrap 236 may likewise include the frictional foam layer along the surface used in the friction pads.

Figure 20:
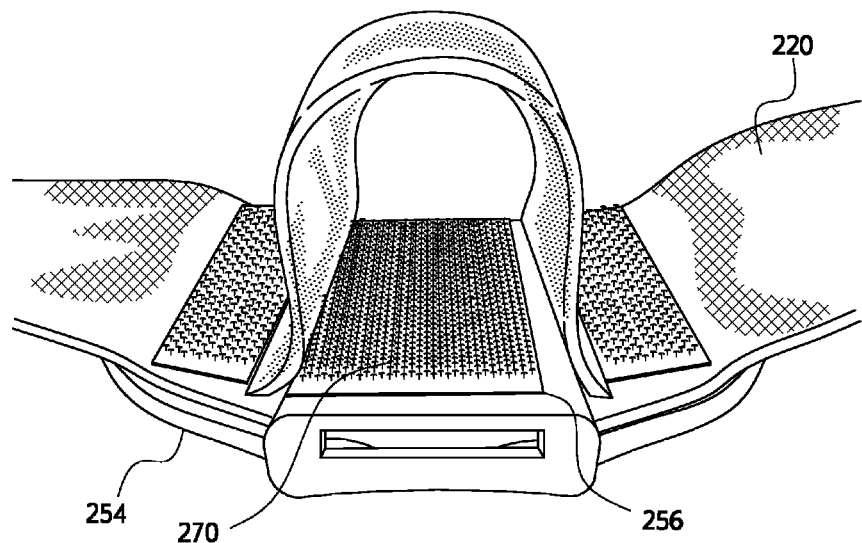
FIG. 20 is a perspective view showing a strap lock for a strap coupling member in the post-operative brace of FIG. 16.

In reference to FIG. 20, a strap coupling member 254 may be in combination with a strap lock 270 located along an inner surface 256, such as along the cuff assembly or strut. The strap lock 270 engages a strap 260 of the strap assembly 220, and mitigates or prevents migration of the strap assembly relative to the corresponding strut.

In the variation depicted in FIG. 20, the lock 270 is preferably in the form of hook material and is placed on the inside of the strut or cuff assembly to face corresponding the loop material of the strap. The lock affixes the strap to the strut, thereby preventing the strap from slipping through the strap coupling members. Prior to first donning the brace on the leg of a wearer, a sheet that does not engage the lock is placed in between this strap and the strap lock which prevents the strap from becoming affixed to the strut while being initially fit to the wearer. Once the straps are set at the right tension on the wearer and the struts are in the proper position, the tabs are removed and the straps affix to the struts. Once affixed, the affixed straps provide enhanced sagittal plane stabilization of the knee.

Not necessarily all such objects or advantages may be achieved under any embodiment of the invention. For example, those skilled in the art will recognize that the invention may be embodied or carried out to achieve or optimize one advantage or group of advantages as taught without achieving other objects or advantages as taught or suggested.

The skilled artisan will recognize the interchangeability of various components from different embodiments described. Besides the variations described herein, other known equivalents for each feature can be mixed and matched by one of ordinary skill in this art to construct an orthopedic device under principles of the present invention. Therefore, the embodiments described may be adapted to orthopedic systems for securing, supporting or comforting limbs or other anatomy.

Although this invention has been disclosed in certain preferred embodiments and examples, it therefore will be understood by those skilled in the art that the present invention extends beyond the disclosed embodiments to other alternative embodiments and/or uses of the invention and obvious modifications and equivalents thereof. It is intended that the scope of the present invention disclosed should not be limited by the disclosed embodiments described above, but should be determined only by a fair reading of the claims that follow.

The invention claimed is:

1. A hinge assembly for an orthopedic device, comprising:
    a pivoting assembly defining a first opening;
    a first strut connected to the pivoting assembly and having a second opening with a shape corresponding at least in part and in location to the first opening;
    a lock body slidably located within the second opening, the lock body defining a groove formed by and along an outer surface of the lock body; and
    a spring located within the groove and arranged to articulate between first and second positions of the lock body relative to the pivoting assembly;
    wherein the groove defines a central narrow portion arranged to retain the spring therewithin in which the spring is biased about the narrowed portion arranged as a fulcrum for flexing between locked and unlocked positions while extending into and biased against walls of the second opening of the first strut.

2. The hinge assembly of claim 1, wherein the groove has an hourglass configuration, the spring articulating between opposed sides of the groove in the first and second positions.

3. The hinge assembly of claim 1, wherein the spring has an elongate, flat configuration across an entirety of its length in a neutral position between the first and second positions.

4. The hinge assembly of claim 1, further comprising a second arm rotatably connected to the pivoting assembly and having at least one notch, the lock body having at least one locking tooth arranged to engage the at least one notch when the lock body is in the second position.

5. The hinge assembly of claim 4, wherein the second arm defines a round head with a plurality of notches formed about the periphery thereof.

6. The hinge assembly of claim 5, further comprising a button securable to the button rod outside of the pivoting assembly.

7. The hinge assembly of claim 6, wherein the pivoting assembly defines an outer cover defining a plurality of indicia, the button arranged to lock at any one of the plurality of indicia.

8. The hinge assembly of claim 1, wherein the lock body defines a button rod extending from a first surface and the pivoting assembly defining a slot arranged for accommodating the button rod in the first and second positions.

9. The hinge assembly of claim 1, wherein the lock body defines at least one stabilizer extending from a second surface, the pivoting assembly including a first plate having at least one slot arranged for receiving the at least one stabilizer as the lock body moves between the first and second positions.

10. The hinge assembly of claim 9, wherein the lock body defines a first stabilizer on a first side of the groove, and a second stabilizer on a second side of the groove.

11. The hinge assembly of claim 1, wherein the first strut defines an elongate strut defining a plurality of adjustment holes.

12. The hinge assembly of claim 1, further comprising a second arm rotatably connected to the pivoting assembly and a round head with a plurality of notches formed about a periphery thereof, the lock body having at least one locking tooth arranged to engage the at least two notches when the lock body is in the second position, the second arm arranged to rotate about a central axis of the pivoting assembly and relative to the first strut.

13. The hinge assembly of claim 12, wherein the pivoting assembly defines flexion and extension stops limiting rotational movement of the second arm relative to the first strut.

14. A hinge assembly for an orthopedic device, comprising:
a pivoting assembly defining a first opening;
a first strut connected to the pivoting assembly and having a second opening with a shape corresponding at least in part and in location to the first opening;
a lock body slidably located within the second opening, the lock body defining a groove formed by and along an outer surface of the lock body; and
a spring located within the groove and arranged to articulate between first and second positions of the lock body relative to the pivoting assembly, the spring having an elongate, flat configuration across an entirety of its length in a neutral position between the first and second positions;
wherein the groove has an hourglass configuration, the spring articulating between opposed sides of the groove past the neutral position in the first and second positions.

15. The hinge assembly of claim 14, wherein the groove defines a central narrow portion arranged to retain the spring.

16. A hinge assembly for an orthopedic device, comprising:
a pivoting assembly defining a first opening;
a first strut connected to the pivoting assembly and having a second opening with a shape corresponding at least in part and in location to the first opening;
a lock body slidably located within the second opening, the lock body defining a groove formed by and along an outer surface of the lock body; and
a spring located within the groove and arranged to articulate between first and second positions of the lock body relative to the pivoting assembly, the spring having an elongate, flat configuration across an entirety of its length in a neutral position between the first and second positions;
wherein the spring is arranged to flex between the first and second positions corresponding to locked and unlocked positions of the first strut relative to the pivoting assembly, the spring is biased about a central narrowed portion of the groove defining a fulcrum for flexing between the first and second positions while extending into and biased against walls of the second opening of the first strut.

17. The hinge assembly of claim 16, wherein the groove has an hourglass configuration, the spring articulating between opposed sides of the groove past the neutral position in the first and second positions.

* * * * *